US008233965B2

(12) United States Patent
Bjørnerud et al.

(10) Patent No.: US 8,233,965 B2
(45) Date of Patent: Jul. 31, 2012

(54) TUMOR GRADING FROM BLOOD VOLUME MAPS

(75) Inventors: Atle Bjørnerud, Oslo (NO); Kyrre Eeg Emblem, Cambridge, MA (US)

(73) Assignee: Oslo Universitetssykehus HF, Oslo (NO)

( * ) Notice: Subject to any disclaimer, the term of this patent is extended or adjusted under 35 U.S.C. 154(b) by 1511 days.

(21) Appl. No.: 11/715,529

(22) Filed: Mar. 8, 2007

(65) Prior Publication Data
US 2008/0221441 A1    Sep. 11, 2008

(51) Int. Cl.
*A61B 5/05* (2006.01)
(52) U.S. Cl. ........................................... 600/425
(58) Field of Classification Search .................. 600/425
See application file for complete search history.

(56) References Cited

OTHER PUBLICATIONS

Wetzel et al., "Relative Cerebral Blood Volume Measurements in Intracranial Mass Lesions: Interobserver and Intraobserver Reproducibility Study," Radiology 2002, 224: 797-803.
Schmainda et al., "Characterization of a First-Pass Gradient-Echo Spin-Echo Method to Predict Brain Tumor Grade and Angiogenesis," AJNR AM J Neuroradiol, Oct. 2004, 25: 1524-1532.
Cao et al., "Clinical Investigation Survival Prediction in High-Grade Gliomas by MRI Perfusion Before and During Early Stage of RT," Int. J. Radiation Oncology Biol. Phys., vol. 64, No. 3, pp. 876-885, 2006.
Emblem et al., "Characterization of Intra-axial Neoplasms by Histogram Analysis of Total Tumor Volume from MR-derived cerebral blood volume maps," Jun. 2006.
Tofts et al., "Quantitative Analysis of Whole-Tumor Gd Enhancement Histograms Predicts Malignant Transformation in Low-Grade Gliomas," Journal of Magnetic Resonance Imaging, 25:208-214, 2007.
Law et al., "Histogram Analysis versus Region of Interest Analysis of Dynamic susceptibility Contrast Perfusion MR Imaging Data in the Grading of Cerebral Gliomas," AJNR Am J Neuroradiol 28:761-766, Apr. 2007.

*Primary Examiner* — Brian Casler
*Assistant Examiner* — Saurel J Selkin
(74) *Attorney, Agent, or Firm* — Knobbe Martens Olson & Bear LLP

(57) ABSTRACT

An embodiment of the invention is to make possible a non-invasive grading of a tumor based on parameters determined from a frequency distribution (histogram) of values in a map representing cerebral blood volume (CBV) or cellular metabolism in the tumor. The method is especially applicable to brain tumors such as gliomas where histological grading is difficult. The invention provides a precise and consistent grading since it relies on values selected from the whole tumor (not just from hot spots); since it takes the diversity or heterogeneity of the vascularization into account by analyzing the frequency distribution (not just a mean value); and since it involves and allows for a more automated procedure wherein any subjective contributions from human operators is not critical to the resulting grading. CBV maps may be obtained by perfusion imaging using MRI or CT scanning. Cellular metabolism maps may be obtained from a glucose metabolism map obtained by positron emission tomography (PET).

25 Claims, 9 Drawing Sheets

TUMOR GRADING FROM BLOOD VOLUME MAPS

FIELD OF THE INVENTION

The present invention relates to tumor grading, in particular tumor grading by analysis of blood volume maps obtained by e.g. perfusion imaging using contrast agents.

BACKGROUND OF THE INVENTION

It is often of interest to locate and characterize tumors in a non-invasive manner, this is especially relevant for brain tumors (gliomas) due to their inherent inaccessibility. Here, MRI (Magnetic Resonance Imaging) and CT (Computed tomography) imaging are typically the imaging methods of choice. While being excellent for determining position and size, these techniques convey little information about the functional status of the tumor tissue or adjacent tissue (e.g. degree of angiogenesis, tissue viability, malignancy, etc). Although tumor malignancy to some extent may be suggested indirectly by contrast enhanced imaging, several studies have shown that the degree of contrast enhancement is by no means a reliable indicator of tumor grade. Based on these shortcomings, dynamic susceptibility perfusion imaging is becoming increasingly important due to its usefulness in physiological imaging.

Perfusion imaging of tumors is used to demonstrate the vascular growth (angiogenesis and neovascularization) associated with tumor growth by imaging the Blood Volume (BV) or Blood Flow (BF) in a tumor. Since BV values correlate with the grade of vascularity; high-grade (malign) tumors tend to have higher BV values than low-grade (less malign) tumors. Perfusion imaging is therefore helpful in the grading of tumors. Imaging methods for mapping the cellular metabolism may correlate with the grade of vascularity in a similar way, and may therefore also be used.

Several studies have shown to differentiate between high- and low-grade gliomas based on relative cerebral blood volume (rCBV) maps obtained by perfusion MRI. The general way to characterize glioma malignancy is by measuring the ratio between the most elevated rCBV area within the glioma ("hot-spot"), and an unaffected contra-lateral white matter rCBV value. Although several notations are used, this ratio is often referred to as normalized CBV (nCBV), and high-grade gliomas tend to have a higher nCBV ratio than low-grade gliomas. This method is described in e.g. Wetzel et al., Radiology 2002: 224: 797-803.

However, there are several limitations to this method. First, the selection of glioma hot-spot is highly user-dependent and differentiation between vessels and tumor region of true blood volume elevation can be challenging and a source of error. Secondly, since only a few image pixels are typically used to determine the rCBV hot-spot, the method is inherently sensitive to image noise and other sources of spurious pixel values (e.g. spikes introduced by the algorithms used to generate the nCBV maps). Thirdly, unaffected white matter rCBV values are generally used to derive the nCBV value. This is based on the assumption that most gliomas are located in white matter. However, incorrect selection of reference rCBV values might result in either under- or overestimation of nCBV values. Finally, oligodendrogliomas tend to give high nCBV values irrespective of glioma grade.

As a result, cut-off nCBV values between high-grade and low-grade gliomas might be harder to establish if oligodendrogliomas are included. As an alternative to the hot-spot method, Schmainda et al, Am J Neuroradiol 2004: 25: 1524-1532, suggests to use the mean nCBV for the tumor as the basis for grading (referred to as the WT method), but this method has not been consistently compared to the hot-spot method. Also, a mean nCBV has the disadvantage of not reflecting the diversity of values in the tumor.

SUMMARY OF THE INVENTION

It is an object of the present invention to provide a new and more precise approach to tumor grading from BV or cellular metabolism maps.

The invention thus provides a method and a system for grading tumors based on BV or cellular metabolism maps, and a method for preparing a correlation data set to be used in such grading. An overall advantage of the invention is that it is much less dependent on subjective user interaction.

According to a first embodiment, the invention provides a method for grading a tumor on the basis of a map of values representing blood volume or cellular metabolism of a tumor region, the method comprising selecting regions of the tumor whose corresponding values in the map are to be applied in the grading, excluding large blood vessels and areas of necrosis;

defining a plurality of value intervals and counting the number of values of the selected regions within each interval to determine a frequency distribution of values in the selected regions;

assessing a tumor grade based on the frequency distribution, where the more heterogeneous distribution corresponds to a higher grade.

Similarly, in a second embodiment, the invention provides a system for providing parameters to be used in grading tumors, the system comprising software means for co-registering a map of values representing blood volume or cellular metabolism of a tumor region with image data representing tissue type of the tumor region;

a data selection tool for assisting an operator in selecting regions of the tumor whose corresponding values in the map are to be applied in the grading and excluding regions representing large blood vessels and areas of necrosis;

software means for counting the number of values of the selected regions within each of a plurality of value intervals to determine a frequency distribution of values in the selected regions; and means for determining one or more parameters from the frequency distribution related to heterogeneity of the frequency distribution.

The determination of a tumor grade may be carried out by a human operator based on the provided parameters, or may be automated by the system. In the latter case, the means for determining one or more parameters preferably comprises means for correlating said one or more parameters with a grade of the tumor, where the more heterogeneous frequency distribution corresponds to a higher grade.

Also, in a third embodiment, the invention provides a method for preparing a correlation data set for use in assessment of a grade for a tumor by the above method or system, the method comprising:

selecting a set of tumors of similar type so that the set comprises tumors of all grades, providing a histologically determined grade of each tumor in the set;

for each tumor in the set:

selecting regions of the tumor whose corresponding values in the map are to be applied in the grading, excluding large blood vessels and areas of necrosis;

defining a plurality of value intervals and counting the number of values of the selected regions within each interval to determine a frequency distribution of values in the selected regions;

determining one or more parameters characterizing the heterogeneity of the frequency distribution;

correlating the determined parameters with the histologically determined grades to prepare a correlation data set from which a grade can be estimated for another tumor of similar type using corresponding parameters obtained from this other tumor.

A BV map is preferably obtained by perfusion imaging whereby images are acquired before, during and after injection of a contrast agent. When determining BV, the contrast agent is ideally restricted to the vascular system in the tissue of interest in order for its distribution to give a true representation of the blood volume. If the contrast agent distributes throughout the extra cellular fluid space, the determined BV values does not provide a precise estimate of vascularity. All existing MR and CT contrast agents are restricted to the vascuclar space in the brain due to the presence of a blood-brain barrier (BBB). This means that all existing agents are intravascular agents in the brain as long as the BBB is intact. The BBB may be compromised by pathology such as tumours causing contrast agent leakage into the extracellular space. Such leakage may introduce errors in the resulting BV maps. Several methods have been suggested to overcome the errors introduced by such leakage. One method is to fit the first-pass curve to a parametric model like a gamma variate curve (see e.g. Knopp E A et al. Radiology 1999: 21: 791-798). Another method is to apply a pharmacokinetic model to the observed dynamic curves in each voxel and correct for any leakage directly (see e.g. Boxerman J L et al. AJNR 2006: 27: 859-867). Another approach is to use contrast agents with a larger molecular weight so that little leakage occurs even in regions of disrupted BBB. Intravascular contrast agents remain confined to the intravascular space, typically as a result of having a molecular weight of approximately 70,000 and above. Typical types of intravascular contrast agents are Gd-DTPA labelled albumin, Gd-DTPA labelled dextran, and chromium-labelled red blood cells.

Blood volume measurements are meant to determine the volume of blood in a region of tissue. The blood volume (BV) is used to evaluate the micro-vascular density or vascularity, in other words, the density of small blood vessels (capillaries) in a tissue region. Due to relatively small voxel sizes (typically tens of $mm^2$), large vessels in the region could result in a misleading shift of the BV frequency distribution towards higher BV values. Therefore, vessels having dimensions of the order of or larger than the typical spatial resolution of the applied perfusion imaging technique are preferably excluded from the regions whose BV values are used in the data analysis. Similarly, regions consisting of necrotic tissue, if included, shift the BV frequency distribution towards lower BV values, and such regions are preferably also excluded from the regions applied in the analysis.

A cellular metabolism map correlating with the vascularity of the tumor is preferably a glucose metabolism map obtained by positron emission tomography (PET).

The map of values may be a 2D or 3D map resulting from a scanning technique such as perfusion MRI or CT or PET. A 3D map typically consists of several 2D maps representing slices through the tumor region.

The formation of a frequency distribution is also referred to as a histogram analysis, i.e. a mapping that counts the number of observations that fall into various disjoint categories (referred to as bins or value intervals). A histogram (graph or chart) is a typical graphical representation of the histogram analysis or frequency distribution.

The more heterogeneous distribution is the distribution where the values of the map are distributed over more value intervals, thereby representing more tumor volume heterogeneity. The prominence of this characteristic, i.e. the heterogeneity or diversity, however, depends on the number of value intervals and the total number of values, and the more heterogeneous distribution may be described as:

the distribution having the lower maximum value, as this indicates that the values of the distribution (when comparing distributions with the same number of values) are mainly distributed into a broader selection of value intervals and is therefore less peaked.

the distribution having the larger FWHM or similar parameter characterizing the width of the distribution, the wider the distribution, the more heterogeneous it is.

the number of values over a predetermined threshold value interval, as many values in the tail corresponding to large values indicates a spread out and thereby heterogeneous distribution.

The heterogeneity of the frequency distribution or tumor volume, and thereby the grading, may be assessed using several different approaches. Thus, in a preferred embodiment, one or more parameters characterizing the heterogeneity of the frequency distribution, that are to be used in the tumor grade assessment, are on one or more of the following:

a shape of the frequency distribution, variables in a parametric model applied to the frequency distribution, e.g. probability density function or a gamma variate function, the highest relative fraction of values in one interval, corresponding to a peak height in the histogram, whether a significant number of values in the distribution exceed a predetermined threshold or cut-off value (e.g. with $p<0.05$), or a FWHM or similar value of the frequency distribution.

As implied by the third embodiment, the assessment of a tumor grade based in the determined parameters may require having a correlation data set specific to the relevant type of tumors, e.g. brain tumors. This may also allow the grading of the tumor by embodiments of the present invention to be compared with grades obtained by other methods. Thus, the assessment of a tumor grade may comprise comparing the determined parameters with previously determined parameters of equivalent frequency distributions from tumors with a known grading, and using the correlation data set to assess a tumor grade. The system according to the second embodiment may thus comprise data comparison software for this purpose.

As will be described in greater detail in the detailed description, the formation of the frequency distribution may preferably comprise normalizing values of at least the selected regions to a reference value, and normalizing the frequency distribution. Such normalization provides the advantage of enabling comparison between frequency distributions of different tumors obtained at different locations.

A challenge in the method of the invention is to determine the tumor regions from which values are applied in the histogram analysis, this is also referred to as tissue segmentation. The selection of regions is preferably performed in one or more other images where the boundaries of the tumor are more easily determined and different tissue types such as large blood vessels and areas of necrosis more easily segregated. By coregistering such images with the map, values to be applied in the histogram analysis can be selected. Large blood vessels traversing the tumor may give rise to a distorted frequency distribution if included in the selected region. Here, by large is meant larger than voxel size or veins detectable in anatomic (e.g. T2-weighted) images. To provide an as good as possible statistical basis for the parameters determined from the frequency distribution, it would be advantageous to select the entire tumor, less the excluded regions, to be applied in the grading. Hence, this is a preferred feature of the selection.

In one embodiment, the applied regions are selected manually on a slide-by-slide basis by marking up or selecting the regions on appropriate images of the tumor (typically not the BV or cellular metabolism map). In another embodiment, the applied regions are selected by an automated or semi-automated method configured to be carried out by computer software. This provides the advantages of reducing both user dependence and workload.

An analysis of blood volume frequency distributions for high grade tumors has been applied to study the effect of radiotherapy in Cao et al., Int. J. Radiation Oncology Biol. Phys. 2006: 64: 876-885 (doi:10.1016/j.ijrobp.2005.09.001). Here, the temporal changes in CBV frequency distributions of high grade gliomas were studied during radiotherapy to be used as a predictor for survival. The data analysis in this publication does not relate to tumor grading. Only high grade gliomas (grade 3 and 4) are studied Cao et al., which is therefore not considered to be relevant prior art for grading of tumors.

In summary the basic idea of an embodiment of the invention is to make possible a non-invasive grading of a tumor based on parameters determined from a frequency distribution of values in a map representing blood volume or cellular metabolism in the tumor. The grading based on this basic idea is more precise and consistent grading since it relies on values selected from the whole tumor (not just from small specific regions, hot spots); since it takes the diversity of the values into account by analyzing the frequency distribution (instead of simply a mean value); and since it involves and allows for a more automated procedure wherein any subjective contributions from human operators is not critical to the resulting grading.

In the present description, each preferred feature or element may be combined or used by itself and applied to each embodiment, where appropriate. These and other embodiments of the invention will be apparent from and elucidated with reference to the embodiment(s) described hereinafter.

BRIEF DESCRIPTION OF THE FIGURES

The present invention will now be explained, by way of example only, with reference to the accompanying Figures, where.

DETAILED DESCRIPTION OF THE INVENTION

Figure 1:
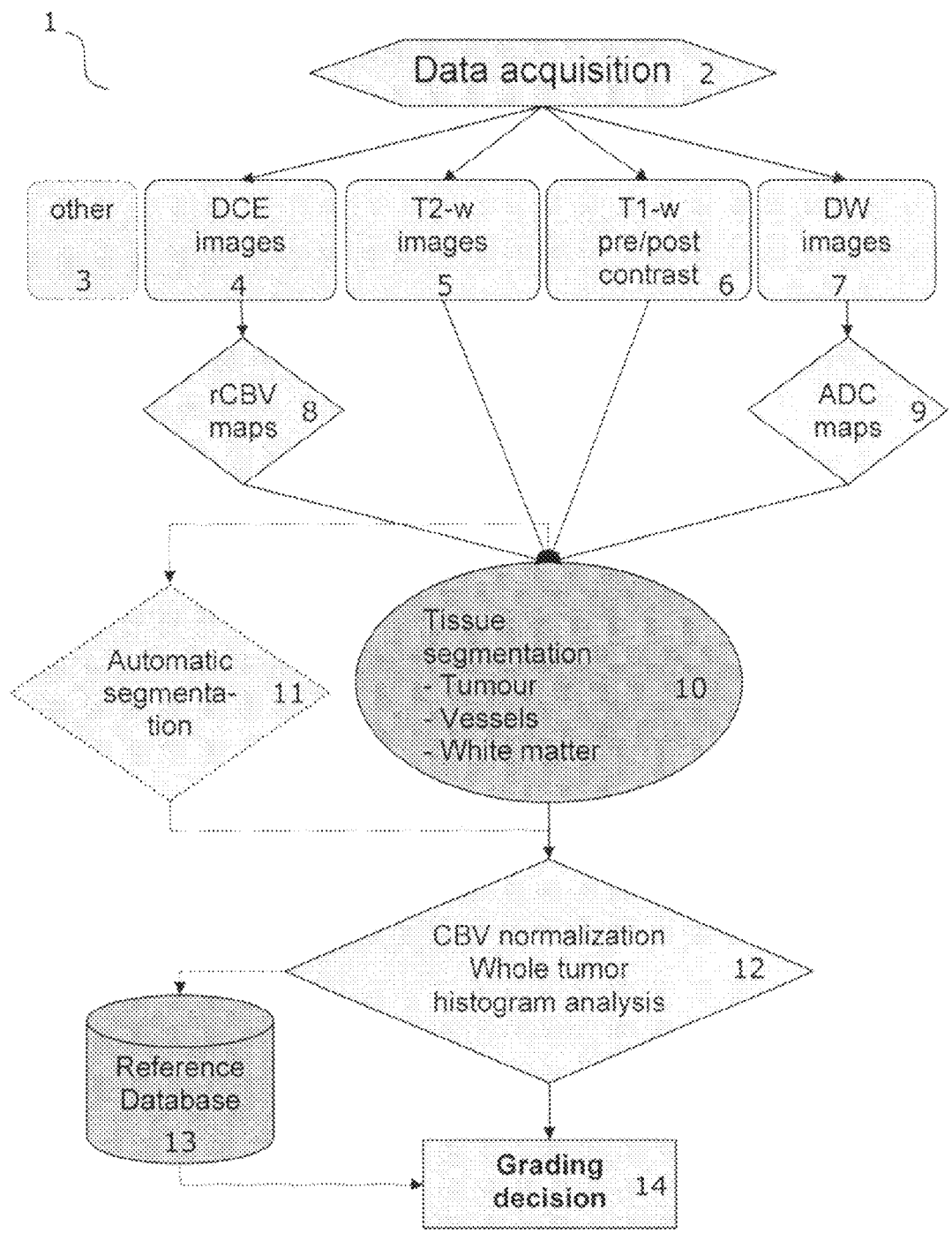
FIG. 1 is a flow diagram illustrating the method and software architecture according to embodiments of the invention.

FIG. 1 is a flow diagram 1 used in the following to embody various embodiments of the invention. The flow diagram 1 outlines and embodies the process steps comprised in the method for grading a tumor according to an embodiment of the invention. The flow diagram 1 outlines and embodies the system architecture, such as software architecture, of the system for providing parameters to be used in grading tumors according to an embodiment of the invention. Also, the flow diagram 1 outlines and embodies the process steps comprised in the method for preparing a correlation data set for use in grading a tumor according to an embodiment of the invention. Although described in relation to the example of CBV maps of brain tumors obtained by perfusion MRI, the corresponding process or architecture can be applied to techniques applied by other embodiments of the invention.

First, the data used to form maps representing blood volume or cellular metabolism and to perform tissue segmentation is acquired in box 1, typically a medical scanning technique such as MRI, CT or PET. The acquired data is used to form images (box 4) used to generate the maps (box 8) and images (box 5 and 6) to be coregistered with the maps to enable selection of regions to be applied in the grading. Other images may be formed if needed (box 3 and box 7).

Obtaining BV data for a tumor by perfusion imaging is a well established technique within the art and has been extensively described. In short, perfusion imaging can be performed by MRI or multi-detector CT scanning by following an intravenously injected bolus of contrast agent. During the first pass of the contrast agent through the vascular system (typically of the order 5 to 15 seconds), it remains in the intravascular space. In MRI perfusion imaging, the intravascular paramagnetic contrast molecules cause a shortening of T2* relaxation, which results in signal loss. Relevant image types include dynamic contrast enhanced (DCE) images, T2-weighted images, T1-weighted images and diffusion weighted (DW) images (boxes 4-7). DCE image are used to generate regional cerebral blood volume (rCBV) maps based on the analysis of the dynamic signal response following bolus injection of the contrast agent (box 8). Apparent diffusion coefficient (ADC) maps (box 9) are generated by analysis of the signal change as a function of diffusion weighting obtained from the DW images. In CT perfusion imaging, the high concentration of the intravascular contrast agent during the first pass causes a higher density. From the changes in signal loss (MRI) or the increase in density (CT), the concentration of the contrast agent in each pixel can be calculated, and a pixel by pixel relative estimate of blood volume can be inferred. Maps of blood volume (BV) and blood flow (BF) can be generated.

Having the required images and maps, the selection of regions of the tumor whose corresponding values in the map are to be applied in the grading can be performed either by an operator (box 10), automatically (box 11) as will be described later, or in a semi-automatic procedure where an operator is assisted in the selection, e.g. by software providing educated guesswork. Large blood vessels and areas of necrosis are sorted out in the tissue segmentation.

Having selected the regions to be applied in the grading, the corresponding values from the maps are used to form the frequency distribution, or histogram, by defining a plurality of value intervals or bins, and counting the number of values of the selected regions within each bin (box 12). When forming the histogram, an appropriate number of intervals or bins should be selected. Having too many would result in too "flat distribution" with very few or none values in each bin. Having too few would result in a very peaked distribution regardless of the heterogeneity of the values. Often, one the following rules may be used to determine the number of bins, N, from the number of data points, n, here the number of BV values (voxels) in the tumor regions selected to be applied in the analysis:

$$N = A\sqrt{n}$$

$$N = 10 \log n$$

Here A is a constant that may be determined for one sample to give a suitable frequency distribution for the purpose of determining the grading, whereafter the equation can be used to scale the number of bins for different data sets.

Further in box 12, the individual values are normalized against values from normal tissue in the same subject, or against a standard reference value. Reference tissue can be obtained by several means. First, it can be obtained by manual selection by a trained user. Alternatively it can be obtained by automated methods whereby the unaffected white matter of the brain is automatically segmented out using established segmentation techniques. Finally, standardization can be achieved by relating the rCBV to the arterial input function; e.g. the first-pass response in an artery feeding the relevant parts of the brain tissue. The arterial input function can be selected manually or automatically using appropriate segmentation techniques. This will be described later in relation to a more detailed example. Also the frequency distribution itself can be normalized so that the area under the resulting histogram curve equals 1.

The resulting histogram can be evaluated in different ways to estimate a grade of the tumor. An experienced radiologist that has evaluated a large number of such histograms can estimate a tumor grade directly from the normalized histogram. This is indicated by the arrow between boxes 12 and 14. Hence, in one embodiment, the system may simply present the histogram to the operator.

In another embodiment, one or more parameters characterizing the heterogeneity of the frequency distribution, e.g. by the shape, peak height, width, etc. of the histogram, can be determined. Hence, in another embodiment, the system may present a parameter characterizing the vascularization heterogeneity of the tumor to the operator. Examples of parametric functions that could be used include the gamma variate function:

$$F(rCBV) = rCBV^a \exp(-rCBV/b)$$

where a and b are model parameters and rCBV is the regional blood volume (or normalized blood volume). Another example could be a Gaussian function of the form:

$$F(rCBV) = \exp\left[-\frac{(rCBV - K)^2}{a^2}\right]$$

where a and K are model parameters. For both these examples the peak height and the FWHH of the distribution can be expressed analytically in terms of the model parameters.

According to one embodiment of the invention, histograms as described in the above are formed for a set of tumors that has also been graded histologically, which can serve as a reference database (box 13) for the grading of tumors. By correlating the distributions, typically through the determined parameters, with the histologically determined grades, a correlation data set can be prepared. Using the correlation data set, a grade can be estimated for a new tumor of similar type using corresponding parameters obtained from this new tumor. Hence, in yet another embodiment, the system may present an estimated grade to the operator.

Figure 2:
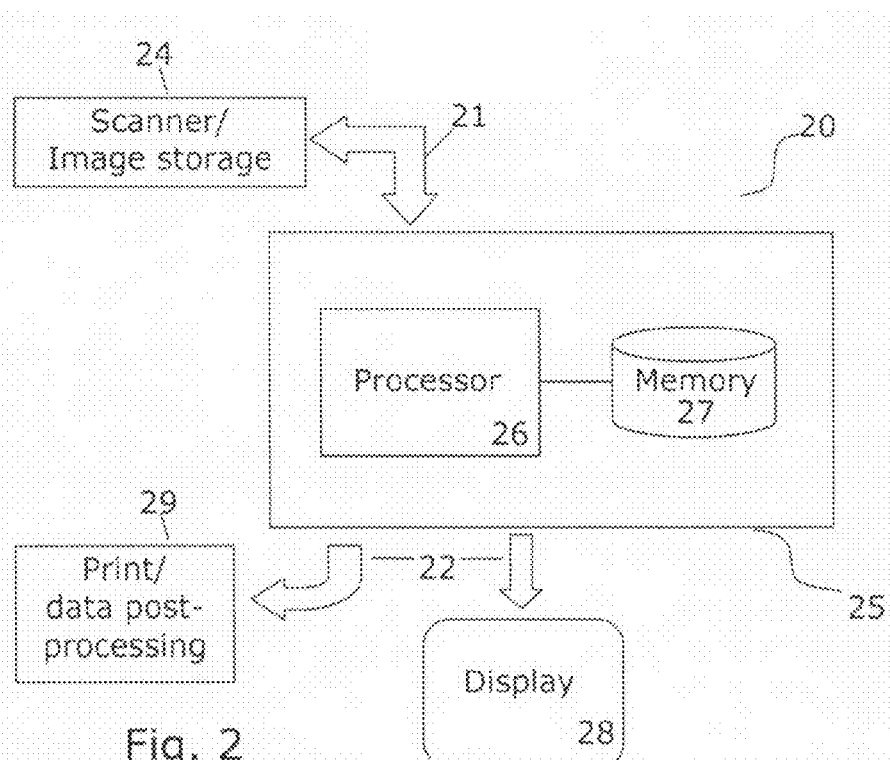
FIG. 2 is an illustration of a layout of a system for grading tumors, for performing histogram analysis, for preparing a correlation data set, or for performing automated segmentation of tissue to selected tumor regions in accordance with various embodiments of the invention.
Figure 3A:
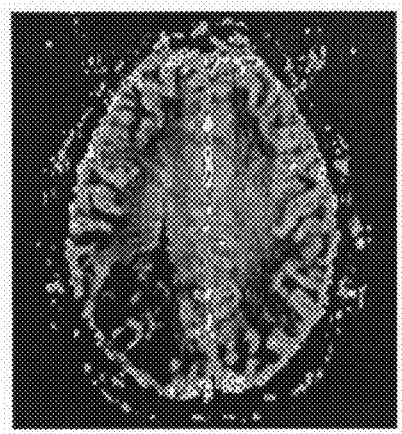
FIGS. 3A-D show a sample case of a patient with a grade II diffuse astrocytoma (Subject 120, Table 1) demonstrating the use of nCBV overlay maps to identify vessels within the tumor region.
Figure 3B:
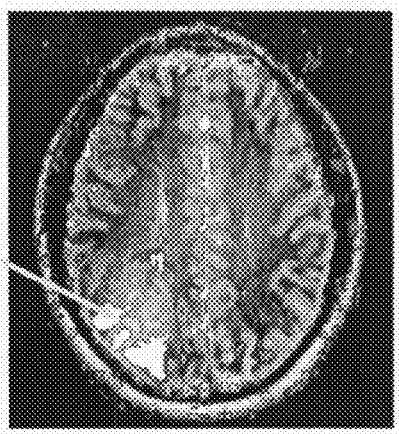
Figure 3C:
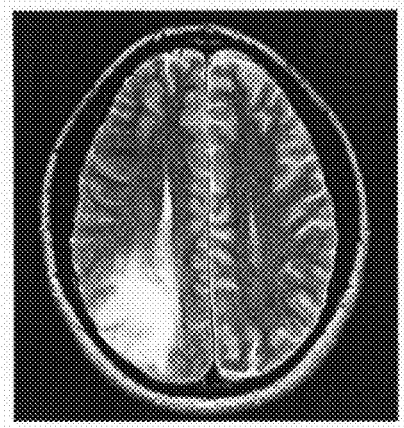
Figure 3D:
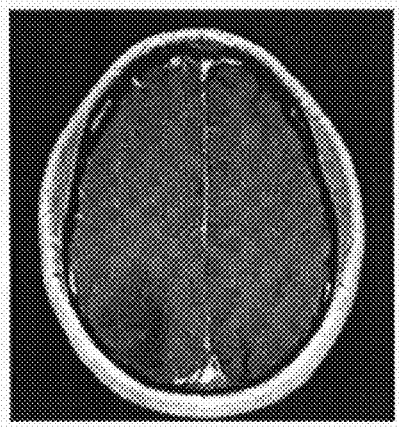

FIG. 2 illustrates a hardware layout of a system 20 for grading tumors, for performing histogram analysis, for preparing a correlation data set, or for performing automated segmentation of tissue to selected tumor regions in accordance with various embodiments of the invention. The system 20 has means 21 for receiving or accessing image data to be processed from an image recording apparatus such as a CT, MR, or PET scanner 24. Alternatively, 24 may represent an internal or external storage holding images recorded by such apparatus. The means 21 may e.g. be a data bus allowing access to a memory, an internet connection, or a cable or wireless connection. The system comprises a computer 25 or a similar processing apparatus holding an electronic processor 26 and memory 27 for holding and executing computer programs applying algorithms for tissue segmentation, histogram analysis and/or grading using the received image data, such as BV maps containing BV values and other contrast images for identifying and selection relevant tumor regions. A possible architecture for such software is described in relation to FIG. 1 in the above. After processing the received image data, the resulting histogram, parameter, or tumor grade could be applied in further (post)processing or displayed, printed etc. The system therefore also has means 22 for transmitting the result to a display 28, a printer, or to a further processing 29, e.g. a cable, data bus, internet connection or similar.

In the following, an application of the method according to an embodiment of the invention is described in relation to a method for glioma grading based on MR-derived cerebral blood volume (CBV) maps. The method is directly compared to the hot-spot method applied in the prior art. The description provides further details of the image recording and the histogram analysis and serves to further enable the invention.

Fifty patients (mean age 46 years, range 6-76 years, 28 males, 22 females) with histologically confirmed gliomas were imaged using dynamic contrast-agent enhanced magnetic resonance (MR) imaging. Imaging was performed at 1.5 Tesla (Siemens Sonata, Symphony or Avanto, Siemens AG, Erlangen, Germany). Imaging was performed using a 8-channel—(Symphony/Sonata) or a 12-channel (Avanto) headcoil. The protocol included axial T2-w fast spin-echo (FSE) (TR/TE, 4000 ms/104 ms) and axial T1-w spin-echo (SE) (TR/TE 500 ms/7.7 ms) obtained before and after i.v. administration of contrast agent.

The voxel size was $0.45 \times 0.45 \times 5$ mm$^3$ with 19 slices in both sequences. Dynamic contrast-enhanced perfusion MRI was performed using a gradient-echo echo-planar imaging (GRE-EPI) sequence acquired during contrast agent administration. The imaging parameters were: TR/TE 1430 ms/46 ms, bandwidth 1345 Hz/pixel (12 axial slices) or 1720 ms/48 ms, bandwidth 1500 Hz/pixel (14 axial slices), voxel size $1.80 \times 1.80 \times 5$ mm$^3$ and inter-slice gap of 1.5 mm. The number of slices was adjusted to cover the entire lesion. For each slice, 50 images were recorded at intervals equal to TR. After approximately 8 time-points, 0.1 mmol/kg of Gadovist (Schering AG, Berlin, Germany) was injected at a rate of 5 mL/sec, immediately followed by a 20 mL bolus of saline (B. Braun Melsungen AG, Melsungen, Germany) also at 5 mL/sec.

The images were transferred to a workstation and post processed using a dedicated software package (nordicICE™, NordicImagingLab, Bergen, Norway). The rCBV maps were generated using established tracer kinetic models applied to the first-pass data. To reduce the effects of recirculation, the $\Delta R2^*$ curves were fitted to a gamma-variate function which is an approximation of a $\Delta R2^*$ curve as it would appear in the absence of recirculation or leakage. nCBV maps were calculated on a pixel-by-pixel basis by dividing every rCBV value in a specific slice with an unaffected white matter rCBV value defined by a neuroradiologist. The nCBV maps were displayed as color overlays on the structural images. Coregistration between the conventional MR images and the nCBV maps was performed based on the geometric information stored in the respective datasets. If needed, the nCBV overlay map was interactively adjusted to optimally match the two datasets.

Figure 4A:
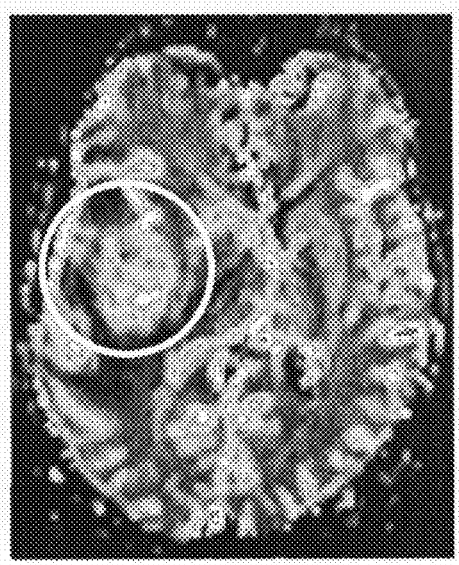
FIGS. 4A and B show rCBV maps of a glioblastoma (A) and low grade oligoastrocytoma (B), the white circles indicate the tumor region in which regions to be applied are selected.
Figure 4B:
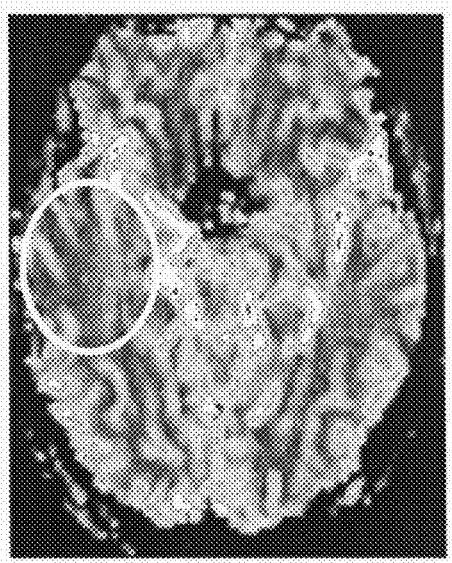

All evaluations were performed independently by four experienced neuroradiologist familiar with perfusion MRI. A transparency slider for the overlay was interactively adjusted to identify large vessels as well as regions of contrast enhancement, necrosis or edema from the T1-w and T2-w underlay images. FIGS. 3A-D show a sample case of a patient with a grade II diffuse astrocytoma (Subject 120, Table 1) demonstrating the use of nCBV overlay maps to identify vessels within the tumor region; 3A shows a nCBV map. 3B shows coregistered nCBV map overlaid on a T2-w FSE image (TR=4000/TE=104). 3C shows a T2-w FSE image. 3D shows a post-contrast T1-w SE image. The red arrow in 3B indicates a potential hot-spot area as seen on the nCBV map. However, the underlying "vessel-like structure" identified in both the T2-w image (3C) and the post-contrast T1-w image (3D) might suggest that this is not a true hot-spot. FIGS. 4A and B show rCBV maps of a glioblastoma (A) and low grade oligoastrocytoma (B), the white circles indicate the tumor region in which regions to be applied are selected. The higher heterogeneity and larger peak nCBV values are reflected in the corresponding histograms shown later in FIG. 7.

Region of interests (ROIs) were drawn on the nCBV overlays according to the combined overlay/underlay information. Three methods for glioma grading were tested in each subject; the method according to an embodiment of the invention (referred to as the histogram method in the following), the WT method described in Schmainda et al (Am J Neuroradiol 2004: 25: 1524-1532) and the hot-spot method described in Wetzel et al. (Radiology 2002: 224: 797-803).

Figure 5A:
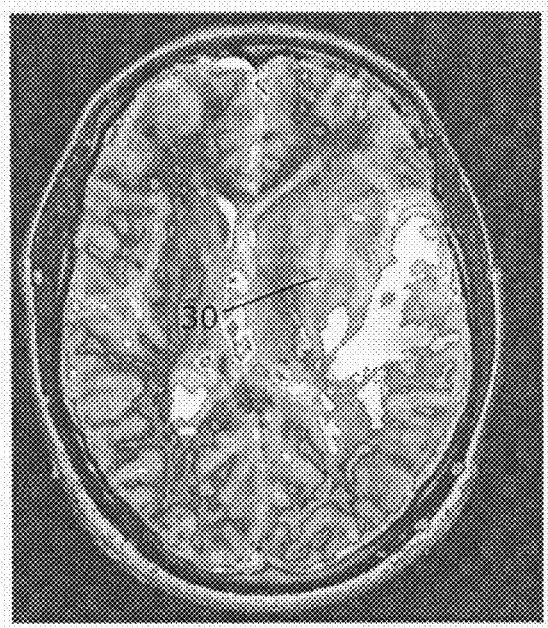
FIGS. 5A and B show the glioma delineation marked by a thin grey line 30 on different images of a grade II oligodendroglioma.
Figure 5B:
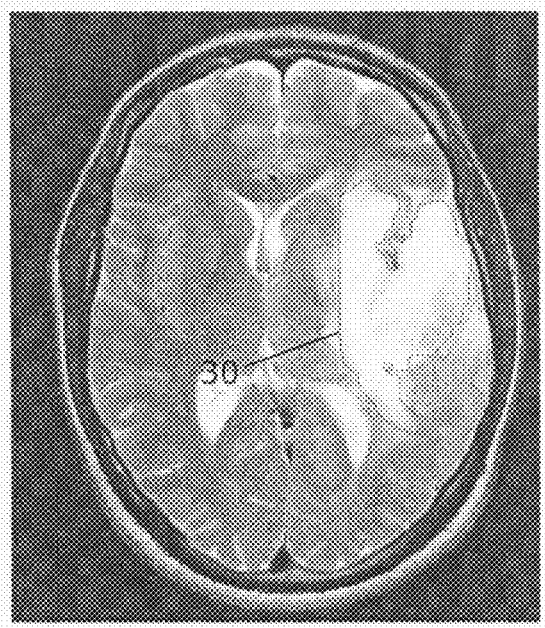

The histogram method in accordance with an embodiment of the invention was carried out as described in the following. Using the available information in the different image sets, the observers selected regions of the tumor whose corresponding values in the map are to be applied in the grading, excluding large blood vessels and areas of necrosis. The selection was made by drawing freehand ROIs of what was considered to be the complete tumor area in each slice. FIGS. 5A and B demonstrate the glioma delineation, here marked by a thin grey line 30 on a grade II oligodendroglioma. FIG. 5A shows it on a coregistered rCBV map overlaid on a T2-w FSE image (TR=4000/TE=104), FIG. 5B shows it on a T2-w FSE image (TR=4000/TE=104). As seen in both images, the observer has taken care to avoid areas within the glioma region with low signal on the T2-w image and high signal on the nCBV map which was thought to represent blood vessels.

Frequency distributions in the form of histograms were generated by classifying the nCBV values in the selected regions into a given number of bins. The area under the resulting histogram curve was normalized to 1. The range of the nCBV values along the x-axis was kept constant (0-15). The histogram method was tested using 5, 15, 25, 35, 50 or 100 bins. Glioma malignancy was assessed by measuring the maximum normalized peak height of the distribution (i.e. relative frequency of nCBV values in a given histogram bin), under the hypothesis that the peak height of the histogram distribution is inversely proportional to CBV heterogeneity, and hence tumor malignancy.

In the hot-spot method, each observer selected a minimum of four ROIs which was believed to represent high nCBV regions and the maximum value was used. In the case of multiple lesions, the largest lesion was chosen. In compliance with the reference method, the size of the tumor ROIs were kept constant (circular ROI with radius 1.8 mm). Finally, a mean nCBV was generated based on the total tumor volume as defined by the four observers (WT method).

Mann-Whitney tests were used to evaluate the glioma grading capability of each method. A significance level of P=0.05 was used for all tests. Sensitivity and specificity, based on optimal cut-off values, were derived using binary logistic regression. A glioma classified as high/low-grade by both observer data and histology was considered as a true-positive/true-negative findings, respectively. To compare our results with previous studies, the sensitivity and specificity of the hot-spot method was also calculated using a previously published cut-off nCBV value of 1.75 (15). The ability of each method to differentiate between grade II oligodendroglial tumors (oligodendrogliomas or oligoastrocytomas) and grade II diffuse astrocytomas, or between grade III gliomas (anaplastic) and grade IV gliomas (glioblastoma) were investigated. Inter-observer reproducibility with respect to glioma grading was tested by assessing the percentage of patients in which the data from all observers gave the same glioma grade. This was tested for each method using the optimal cut-off values estimated by binary logistic regression. For the hot-spot method, this percentage was also estimated using the proposed 1.75 cut-off value. Statistical analysis was performed using SPSS 13 (Apache Software Foundation, Chicago, US).

Figure 6A:
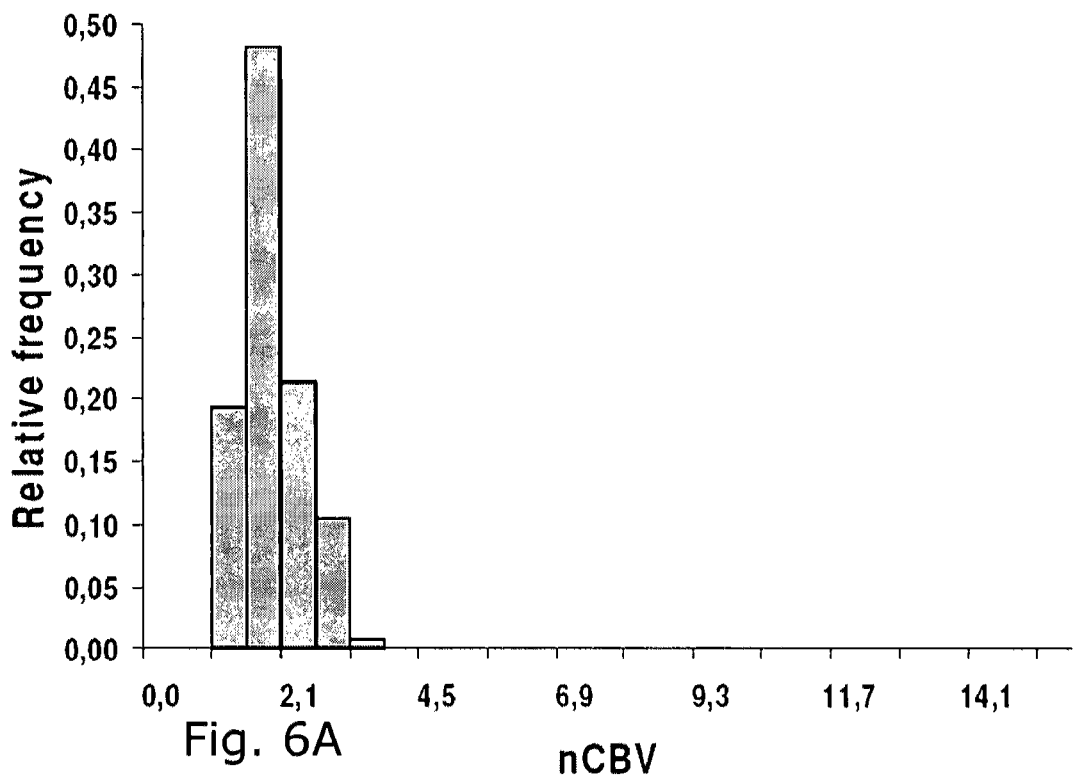
FIGS. 6A and B are 25-bin histograms illustrating the distribution of nCBV values in total glioma volume of (A) grade II diffuse astrocytoma and (B) grade IV glioblastoma. Note the low maximum peak height and wide distribution in (B) compared to (A).
Figure 6B:
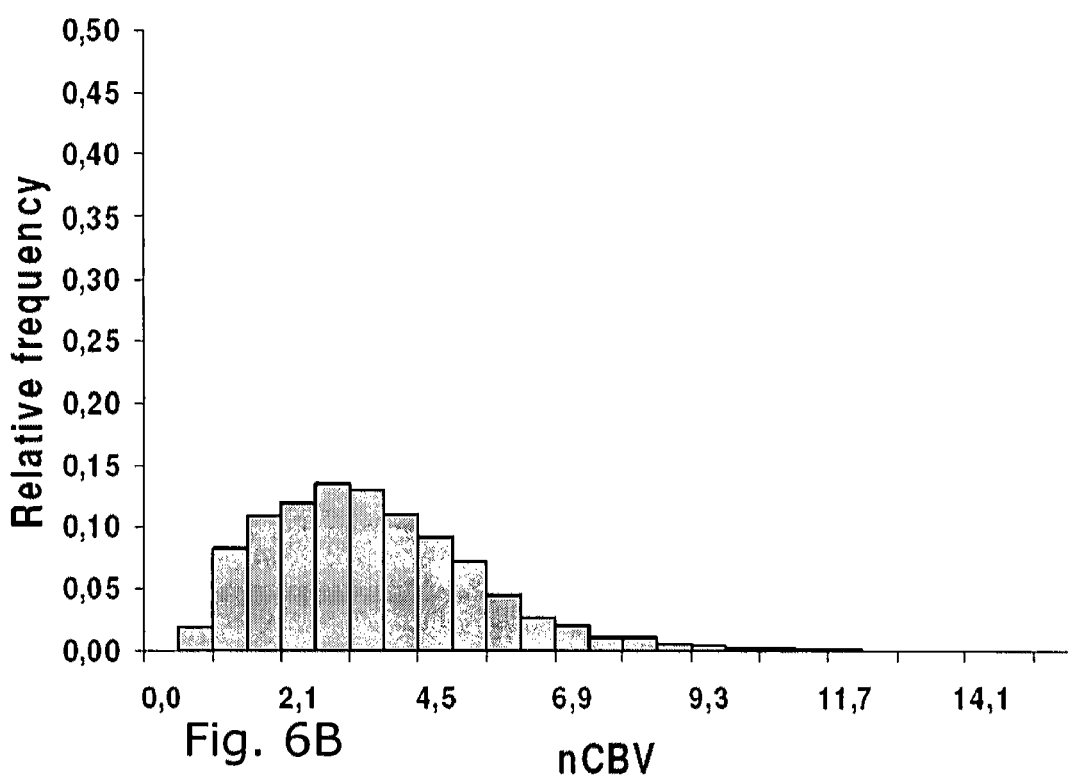
Figure 7:
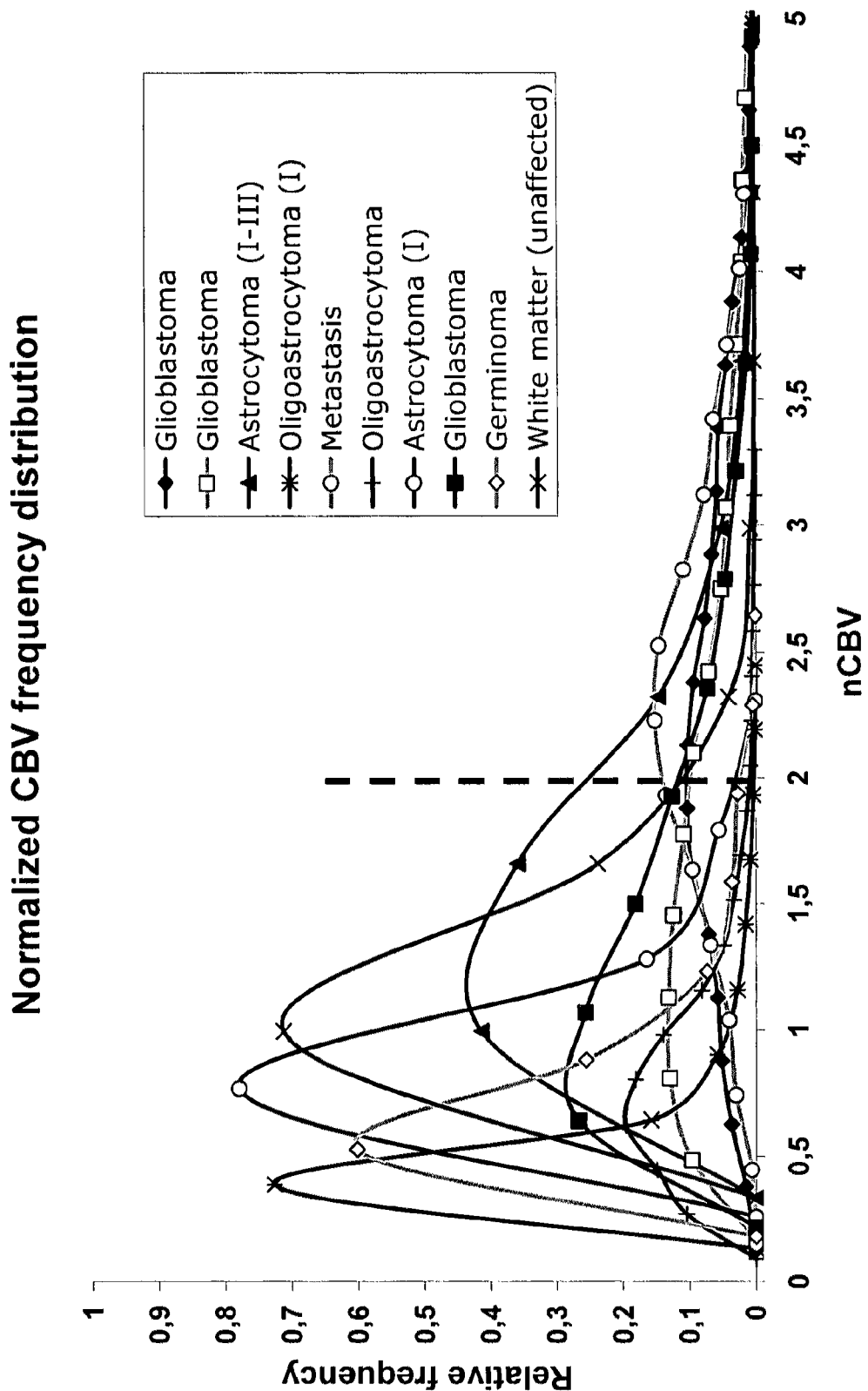
FIG. 7 shows the histogram distribution of nCBV values in a number of investigated tumors.

Of the 50 gliomas investigated, 27 were histologically confirmed to be low-grade (WHO grade I-II) and 23 were high-grade (WHO grade III-IV). A summary of patient demographics, histological diagnosis, surgical procedure and conventional MR findings are shown in Table 1 in the appendix. On average, the four observers reported using 7 minutes and 11 minutes per patient when using the hot-spot method and tumor delineation (WT and histogram method), respectively. The methods were reported equally difficult to perform. FIGS. 6A and B are 25-bin histograms illustrating the distribution of nCBV values in total glioma volume of (A) grade II diffuse astrocytoma and (B) grade IV glioblastoma. Note the low maximum peak height and wide distribution in (B) compared to (A). FIG. 7 shows the histogram of the frequency distribution of nCBV values in a selection of investigated tumors. A cut-off or threshold nCBV value of 2.0 ($p<0.05$) as shown by the vertical punctured line was found to differentiate high-grade tumors from low-grade. Note the distinct shape difference between the high-grade and low-grade tumors.

As shown in Table 2 in the appendix, all methods tested could correctly identify high-grade (grade III and IV) gliomas ($P<0.001$, $P<0.006$ and $P<0.001$ for histogram-, hot-spot- and WT-methods, respectively). Regardless of bin numbers, only the histogram method was able to differentiate between grade III (n=5) and grade IV gliomas (n=18) in all observers (Table 3 in the appendix).

Figure 8A:
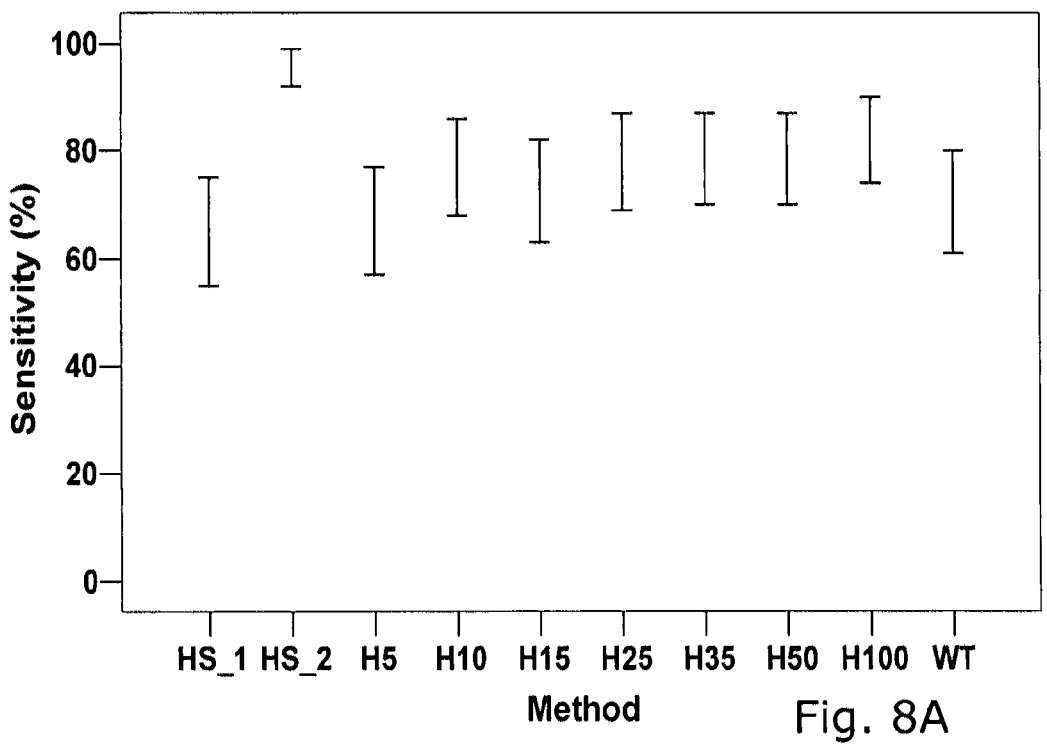
FIGS. 8A and B show confidence-intervals for the sensitivity (A) and specificity (B) of the hot-spot method (HS_1 and HS_2), the histogram method with different number of bins (H5-H100), and the WT method (WT).
Figure 8B:
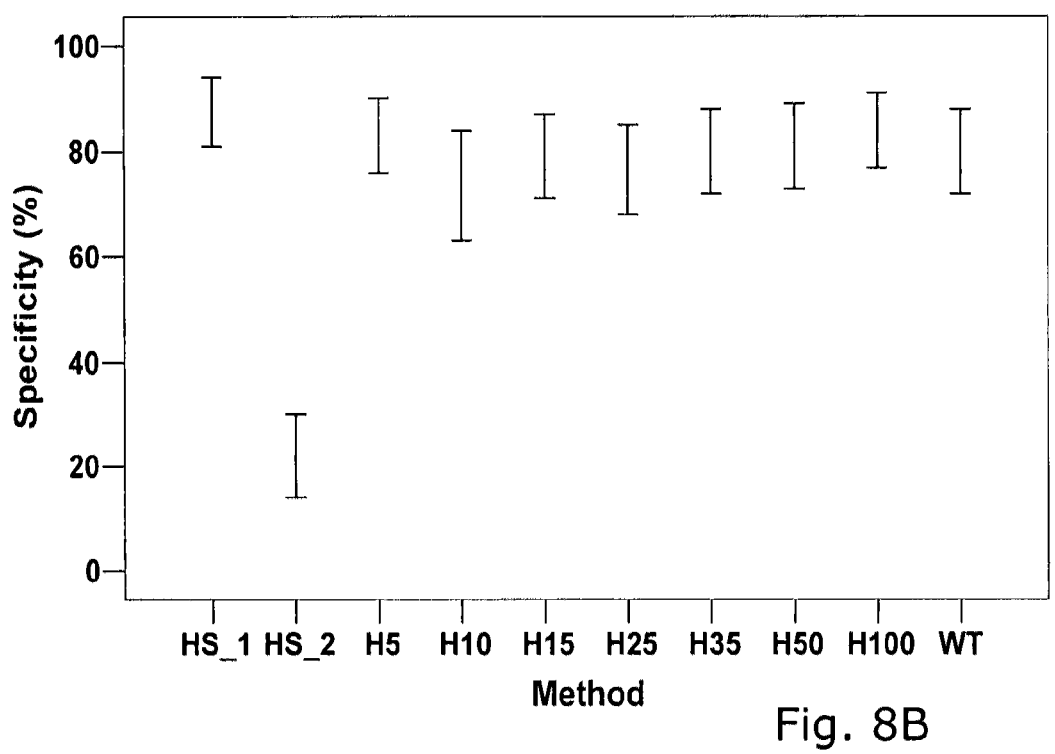

For all methods and all histogram bin numbers, there was an overlap between the 95% confidence-intervals for both specificity and sensitivity in all observers. Hence, the confidence-intervals were considered similar, and the data could be pooled, giving 200 data points for each method (Table 3). Using optimal cut-off values, the sensitivity of the histogram method (100-bins) was borderline significantly higher than the sensitivity of the hot-spot method (74-90% vs. 55-75%, respectively). The sensitivity using a nCBV cut-off value of 1.75 was significantly higher than any other method (92-99%), and the specificity was significantly lower (14-30%). FIGS. 8A and B show the resulting confidence-intervals for the sensitivity (A) and specificity (B) of the hot-spot method using an optimal cut-off value (HS_1), the hot-spot method using a published cut-off value of 1.75 (HS_2), the histogram method with different number of bins (H5-H100), and the WT method (WT). Agreement in glioma grade based on data from all observers was obtained in 68%, 82% and 88% of the patient population when using the hot-spot, WT and histogram method, respectively (Table 3).

Using optimal cut-off values, the results show that the histogram method according to an embodiment of the invention is less user-dependent than the hot-spot method and provides significantly higher sensitivity and equal specificity. Further, the histogram method may be made independent of choice of reference tissue. The effect of changing the reference tissue from e.g. white to gray matter is simply a shift of the position of the peak distribution bin without changing the actual peak value. In contrast, the hot-spot method is critically dependent on correct selection of reference tissue since the determination of nCBV is based on this parameter alone. Although the number of histologically confirmed grade III gliomas was low in this study (n=5), only the histogram method was able to differentiate between grade III and grade IV gliomas (Table 3). The consistent results of the histogram method suggests that grade IV gliomas are generally more heterogeneous than grade III gliomas, whereas both grade III and IV gliomas might have similar hyper-vascular regions. As described in previous studies (18), necrosis was a specific marker for distinguishing grade IV gliomas from grade III, but not a sensitive one (Table 1).

Figure 9:
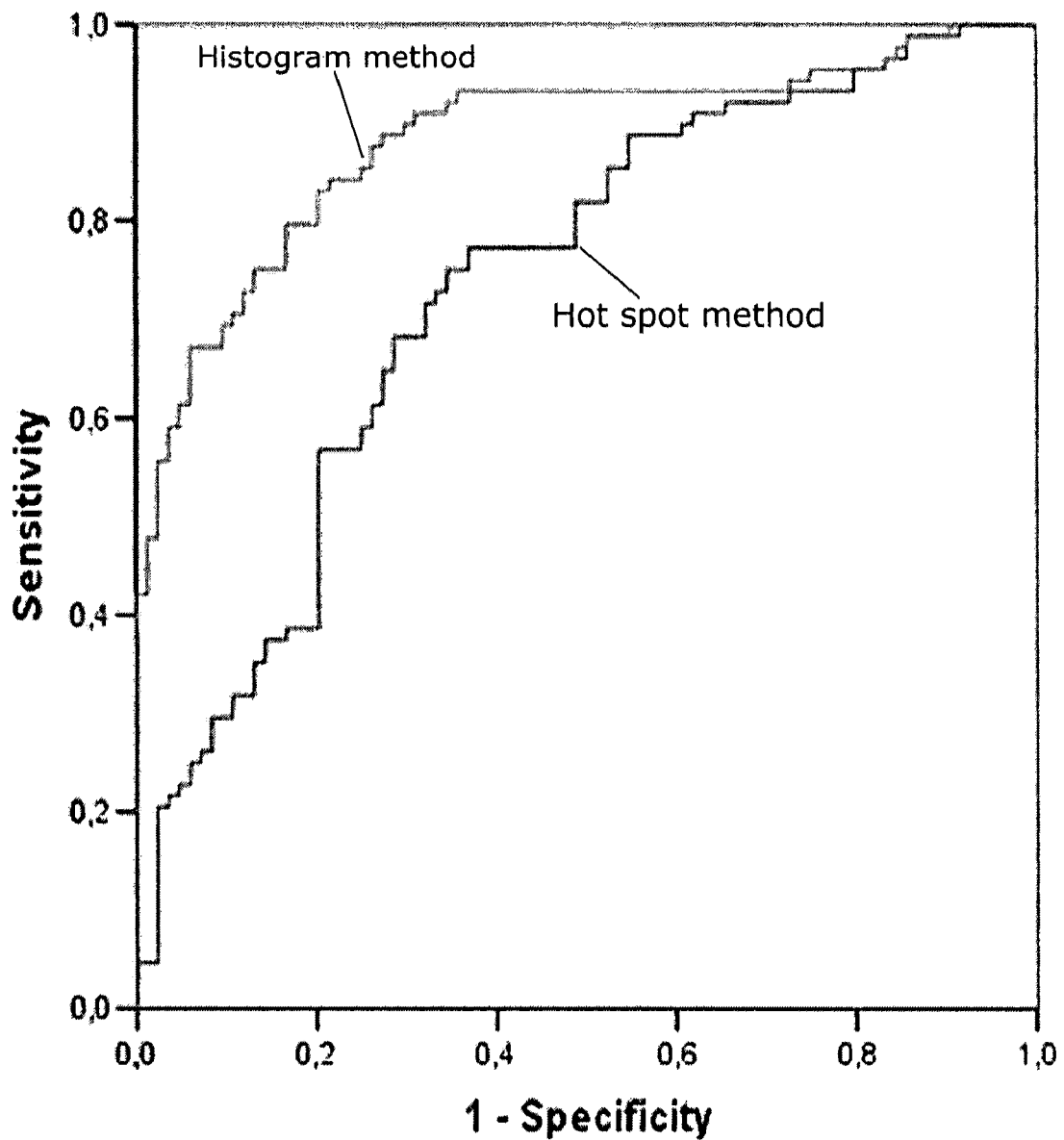
FIG. 9 shows the receiver operator characteristic (ROC) for the histogram vs. the hotspot method.

FIG. 9 shows the receiver operator characteristic (ROC) for the histogram vs. the hotspot method. A ROC is a standard method to assess how sensitivity is affected by changes is specificity. As shown in FIGS. 8A and B, the sensitivity of the hotspot method can be made very high but at the expense of a very low specificity (e.g. many false positives). The histogram method is shown to be a better predictor for glioma malignancy than the hotspot method since the curve is closer to the ideal curve (which would be a single point in the upper left corner; i.e. 100% true positives with no false negatives).

When comparing the use of different histogram bin numbers, the 95% confidence-interval for sensitivity generally improved with increasing number of histogram bins, whereas the specificity remained relatively unchanged (Table 3). The reduced sensitivity at lower bin numbers can be explained by the large range of rCBV values contained in each of the resulting bins which will tend to mask out small hyper-vascular regions in high-grade gliomas.

In the embodiment of the histogram method applied in the above, the peak height of the normalized histogram distribution of nCBV values in the tumor was used as the parameter characteristic for the heterogeneity of the frequency distribution. This approach was chosen because the resulting height is directly dependent on the underlying heterogeneity of the nCBV distribution. As suggested by other embodiments of the invention, the histogram based analysis can be further improved by parametric analysis of the total frequency distribution rather than just the peak value.

According to an embodiment of the invention, the tumor regions from which values are applied in the histogram analysis can be selected by an automated or semi-automated method configured to be carried out by computer software. This provides a more user independent and automated method for selecting regions of the tumor whose corresponding values in the map are to be applied in the grading and for excluding large blood vessels and areas of necrosis. In the below, an automated method that can aid in the selection of tumor regions is described and evaluated. The automated method analyses regions of interest (ROIs) using k-means cluster analysis of multiple MR images taken from a standard CNS tumor image protocol, including first-pass perfusion imaging.

Thirty-five patients with histologically confirmed gliomas, (aged 6-76 yrs, mean age 46; 22 males, 13 females) were included in the study. Imaging was performed at 1.5 T (Siemens Sonata or Avanto, Germany) prior to surgery. rCBV maps were generated using established tracer kinetic models applied to the first pass data obtained by i.v. bolus injection of 0.1 mmol/kg of Gadovist (Schering AG, Germany). The time resolution of the first-pass gradient echo (GRE)-EPI sequence was 1.5 s and the voxel size was $1.8 \times 1.8 \times 6.5$ mm$^3$. An experienced neuroradiologist created normalized (n)CBV maps by dividing each rCBV value in each slice with an unaffected white matter rCBV value. The nCBV maps were coregistered with conventional T2-w FSE, T1-w SE pre-contrast, T1-w SE post-contrast and MR diffusion (b-values=0, 500, 1000) images. K-means cluster analysis was performed in Matlab 2006a by minimizing the squared Euclidean distance between cluster members. The cluster analysis was performed in three steps. Initially, vessels infiltrating the glioma volume were identified by clustering of composite images generated from T2-w and diffusion (DW) images (b=1000, T2-corrected). The resulting images were then used as a binary mask to exclude vessels from further analysis.

Figure 10:
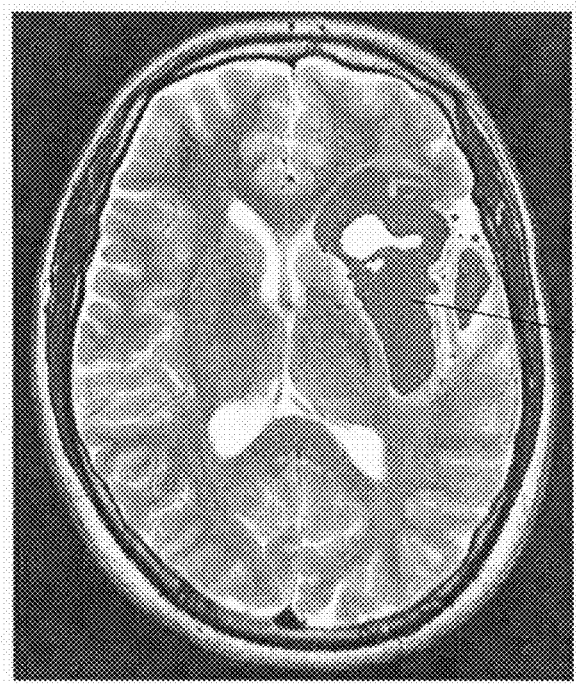
FIG. 10 shows the result of a cluster analysis as an overlay on a T2-w image.

Edema and cystic components were identified from cluster analysis of the DW images alone. The result of these two clustering steps were then used as a mask input to a processed difference image generated from the pre- vs. post contrast enhanced T1-w images to obtain a final estimation of the glioma volume. In FIG. 10, dark grey region 50 is the result of a cluster analysis as an overlay on a T2-w image. The patient was diagnosed with a low-grade astrocytoma. Note the exclusion of both the middle cerebral artery and the cystic components in the centre of the glioma.

The glioma volumes as identified by the process described above were compared to the glioma volumes independently measured by three experienced neuroradiologists blinded to the histopathologic diagnosis. The glioma ROI's were determined from rCBV maps as overlays on the anatomical MR images. Glioma grading was then performed using the histogram method according to an embodiment of the invention, which assesses the maximum normalized peak height of nCBV distribution from the total glioma volume, under the hypothesis that a low peak implies a wide distribution of nCBV values illustrating the heterogeneity of a high-grade glioma. To determine the level of interobserver reproducibility, the results from the independent observers were compared to the results from the cluster analysis using a Mann-Whitney test and a coefficient of variation test. All image analysis was performed using nICE™ (NordicImagingLab, Norway).

Of the thirty-five gliomas investigated, fourteen were histologically confirmed to be high-grade (eleven glioblastoma multiforme [grade IV] and three anaplastic astrocytomas or oligodendrogliomas [grade III]). Of the twenty-one low-grade gliomas, three were pilocytic astrocytomas [grade I] and eighteen were astrocytomas, oligodendrogliomas or mixed oligoastrocytomas [grade II]. The peak nCBV distribution values of the oligodendrogliomas did not differ from the astrocytomas. All three observers obtained statistically significant higher histogram peak values for the low-grade gliomas compared to the high-grade gliomas (Mann-Whitney; p=0.002, p=0.004 and p=0.003). The cluster analysis method gave a more significant difference between the two cohorts (p=0.001).

Figure 11:
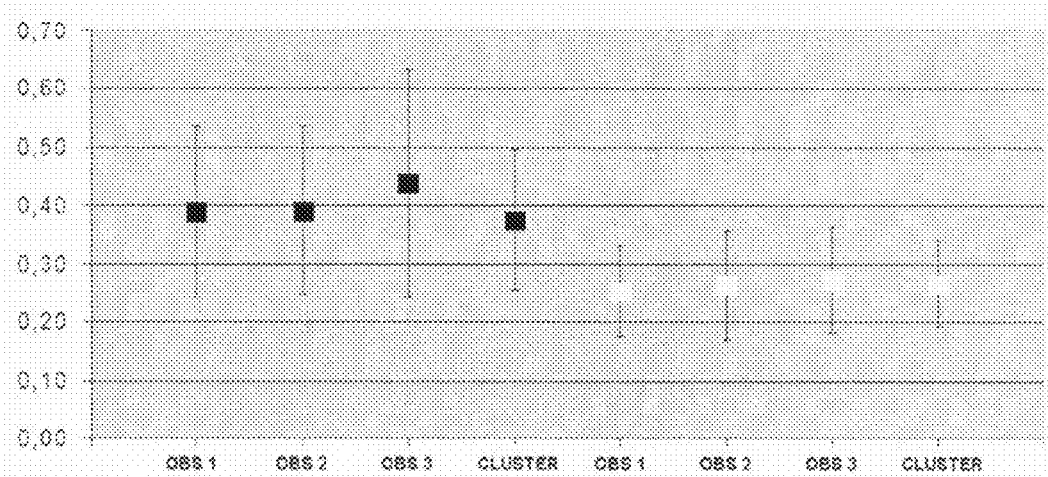
FIG. 11 shows mean nCBV peak values with standard deviations for low-grade (black) and high-grade (light grey) gliomas obtained by observers (OBS) and cluster analysis.

FIG. 11 shows mean nCBV peak values with standard deviations for low-grade (black) and high-grade (light grey) gliomas obtained by observers (OBS) and cluster analysis. Note the reduced relative standard deviation obtained by using cluster analysis compared to the manual selection of total glioma volume (High-grade cohort: 0.34, 0.40, 0.37 for the observers and 0.30 for cluster analysis. Low-grade cohort: 0.38, 0.37, 0.44 for the observers and 0.32 for cluster analysis).

The above study enables the embodiment applying an automated, user independent method to improve delineation of true glioma volume. The method utilizes all available MR data generated in a standard CNS tumor protocol, thereby increasing the likelihood of correct tumor identification in the selection of tumor regions to be applied in the histogram analysis. Although the proposed method has so far been tested in a limited number of patients only, the preliminary results suggest that this method provides a more objective and robust approach compared manual identification of glioma volume.

In the following, one application of present invention is described in relation to evaluating whether oligodendroglial tumors with combined loss of short arm of chromosome 1p (−1p) and long arm of chromosome 19q (−19q) influences the result in glioma grading from MR-derived cerebral blood volume maps. It is a well known problem with the hot-spot method of the prior art that most oligodendroglial tumors exhibit a higher hot spot value than astrocytomas irrespective of WHO grade. It has been suggested that the −1p/−19q genotype might be the reason for this, consequently leading to an inconclusive hot spot grading result. In the study presented in the below, the −1p/−19q genotype influence on grading using the hot-spot method and grading using an embodiment of the invention are compared.

Twenty-two patients with histologically confirmed oligodendrogliomas and oligoastrocytomas (aged 9-62 yrs, mean age 43; 10 males, 12 females) have been included. Loss of heterozygosity (LOH) at 1p and 19q were analyzed using a standard polymerase chain reaction (PCR) technique. Imaging was performed at 1.5 T (Siemens Sonata or Avanto, Germany) prior to surgery. rCBV maps were generated using established tracer kinetic models applied to the first-pass data obtained by i.v. bolus injection of 0.1 mmol/kg of Gadovist (Schering AG, Germany). The time resolution of the first pass gradient echo (GRE)-EPI sequence was 1.5 s and the voxel size was $1.8 \times 1.8 \times 6.5$ mm$^3$. Normalized (n)CBV maps were created by dividing each rCBV value in each slice with a white matter rCBV value obtained from an contra-lateral unaffected region. An experienced neuroradiologist was blinded to the histopathological diagnosis and defined the glioma areas based on the anatomical images (combined with rCBV maps) by drawing freehand regions of interest (ROI's) in each slice. Large tumor vessels were not included in the ROI's. The histogram analysis method according to an embodiment of the invention (histogram method) was used to assess the maximum normalized peak height of nCBV distribution from the obtained total glioma volumes, under the hypothesis that a low peak implies a wide distribution of nCBV values illustrating the heterogeneity of a high-grade glioma. For each glioma, a hot spot (rCBV max) value was also selected using a 16 pixel ROI. All image analysis was performed using nICE™ (NordicImagingLab, Norway). The results from the histogram method were compared to the results from the hot spot method using a Mann-Whitney test and a coefficient of variation test.

Figures 12A, 12B:
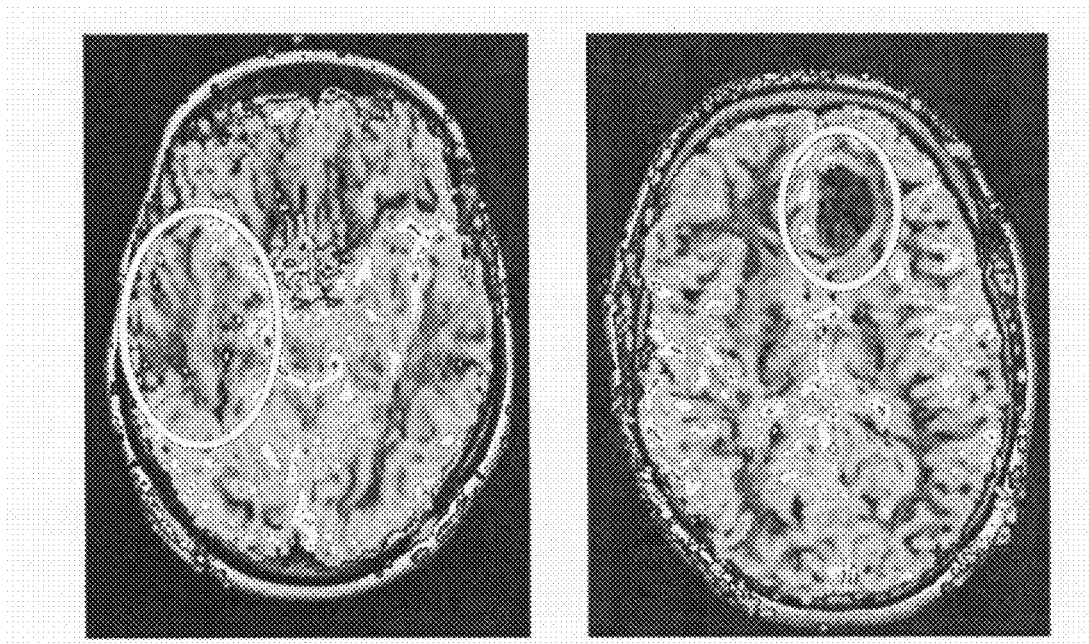
FIGS. 12A and B show examples of nCBV maps of low-grade oligodendroglial tumors (indicated by the white circles) with and without the −1p/−19q genotype.

The −1p/−19q genotype was found in 9 of the twenty-two included tumors. Four gliomas were histologically confirmed as high-grade (grade III), which included two of the nine −1p/−19q genotypes. FIGS. 12A and B show examples of nCBV maps of low-grade oligodendroglial tumors (indicated by the white circles) with and without the −1p/−19q genotype. The rCBV maps are overlaid on T2-w SE images; FIG. 12A shows a low grade oligodendroglioma with −1p/−19q genotype. FIG. 12B shows a low-grade oligodendroglioma without −1p/−19q genotype. Note the low rCBV values in B, typical of gliomas without −1p/−19q genotype.

Figure 13:
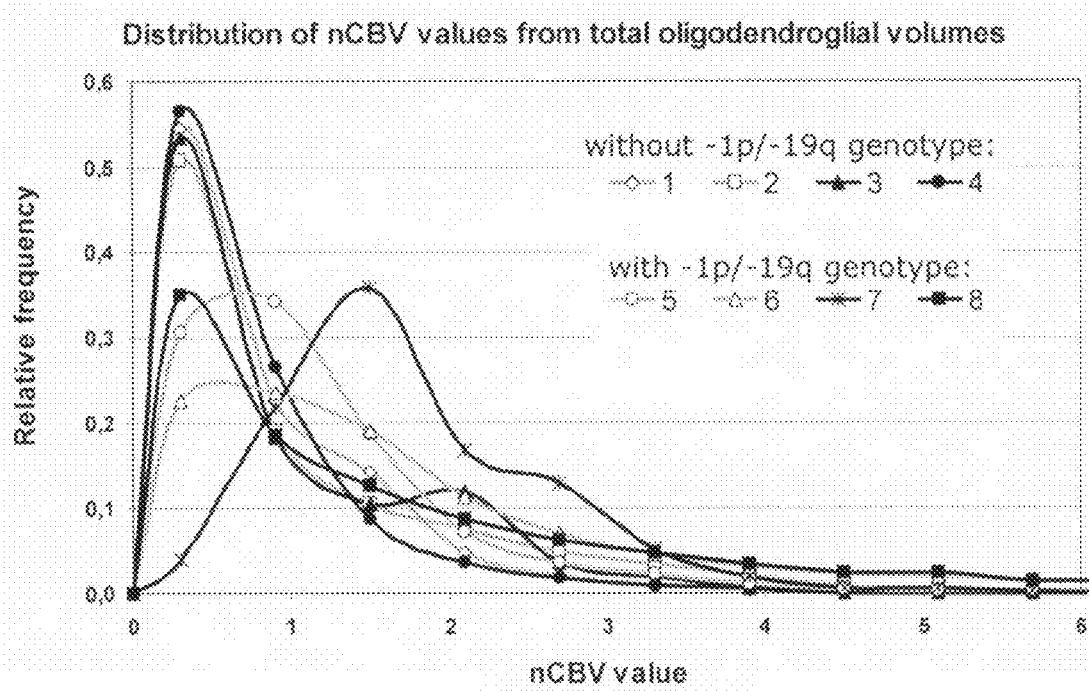
FIG. 13 shows the distribution of normalized nCBV values from total glioma volume in low-grade oligodendroglial tumors without (curves 1-4) and with (curves 5-8) −1p/−19q genotype.

Both the histogram method and the hot spot method were able to differentiate between the low-grade oligodendroglial tumors with and without the −1p/−19q genotype (p=0.003 [histogram] vs. p=0.02 [hot spot]). FIG. 13 shows examples of this when using the histogram method. FIG. 13 shows the distribution of normalized nCBV values from total glioma volume in four low-grade oligodendroglial tumors without −1p/−19q genotype (curves 1-4) and four with −1p/−19q genotype (curves 5-8). Note the lower peak values of the gliomas with the −1p/−19q genotype attributed to increased vascular heterogeneity.

Neither method showed any difference between the four high-grade gliomas, of which two had −1p/−19q genotype. Both methods achieved a statistical significant difference between the low-grade gliomas without the −1p/−19q genotype and the high-grade gliomas (p=0.008 [histogram] vs. p=0.05 [hot spot]), whereas neither could differentiate between the low-grade gliomas with the −1p/−19q genotype and the high-grade gliomas. Including both oligodendroglial tumors with and without the −1p/−19q genotype in the low-grade cohort, only the histogram method achieved a statistically significant difference between the high- and low-grade gliomas (p=0.04). The coefficient of variation was lower for the two low-grade cohorts using the histogram method compared to the hot spot method (with −1p/−19q genotype: 0.33 [histogram] vs. 0.44 [hot spot], without −1p/−19q genotype: 0.16 [histogram] vs. 1.31 [hot spot]).

The results suggest that the presence of −1p/−19q genotype in oligodendroglial tumors strongly influence the results of glioma grading from MR-derived nCBV maps. The hot spot method was less specific than the histogram method for grading high- and low-grade gliomas in the presence of −1p/−19q genotypes, A reason for this might be that even though the low-grade −1p/−19q genotypes show signs of increased vascularity, the distribution of nCBV values in the total glioma volume is still relatively homogeneous. These preliminary results suggest that the histogram method according to an embodiment of the invention provides a more robust approach to glioma grading than the traditional hot spot method.

APPENDIX

TABLE 1

Patent demographics, histological diagnosis, surgical procedure and MR findings.

| Subject | Age (y) | Sex | HD | WHO grade | Surgical procedure | Contrast enhancement | Mass effect | Necrosis | Distant Tumor Foci | Delineation |
|---|---|---|---|---|---|---|---|---|---|---|
| 4 | 41 | M | GB | IV | Biopsy | extensive | extensive | yes | yes | diffuse |
| 5 | 34 | M | DA | II | Biopsy | moderate | extensive | yes | no | diffuse |
| 6 | 41 | F | OA | II | Resection | none | minimal | no | no | diffuse |
| 8 | 61 | F | OD | II | Resection | none | moderate | no | no | diffuse |
| 9 | 35 | F | OA | II | Resection | none | moderate | no | no | diffuse |
| 12 | 27 | M | OA | II | Biopsy | none | moderate | no | no | evident |
| 17 | 75 | F | GB | IV | Resection | extensive | moderate | yes | no | diffuse |
| 18 | 65 | F | GB | IV | Resection | extensive | extensive | yes | no | diffuse |
| 20 | 42 | M | OD | II | Biopsy | moderate | extensive | no | no | diffuse |
| 22 | 50 | M | DA | II | Resection | none | moderate | no | no | diffuse |
| 25 | 24 | F | DA | II | Biopsy | none | extensive | no | no | evident |
| 27 | 62 | M | AOD | III | Resection | moderate | moderate | no | no | diffuse |
| 28 | 48 | M | AOA | III | Resection | extensive | moderate | no | no | diffuse |
| 29 | 53 | F | GB | IV | Resection | extensive | moderate | yes | no | diffuse |
| 31 | 67 | M | GB | IV | Resection | extensive | moderate | yes | no | evident |
| 33 | 64 | M | DA | II | Biopsy | none | moderate | no | no | diffuse |
| 39 | 17 | M | DA | II | Resection | none | extensive | yes | no | diffuse |
| 42 | 18 | F | AA | III | Resection | none | moderate | no | no | diffuse |
| 45 | 53 | M | OD | II | Biopsy | none | minimal | no | no | diffuse |
| 46 | 62 | M | GB | IV | Resection | extensive | moderate | no | no | evident |
| 50 | 43 | F | OA | II | Resection | none | extensive | no | no | diffuse |
| 52 | 58 | F | GB | IV | Resection | extensive | moderate | yes | no | evident |
| 54 | 43 | F | AOA | III | Resection | extensive | extensive | no | no | diffuse |
| 60* | 54 | F | GB | IV | Biopsy | moderate | extensive | yes | no | diffuse |
| 63 | 9 | M | OA | II | Resection | none | minimal | no | no | diffuse |
| 64 | 57 | F | OA | II | Resection | moderate | moderate | no | no | diffuse |
| 66 | 43 | M | OA | II | Resection | none | moderate | no | no | evident |
| 67 | 51 | M | DA | II | Resection | extensive | extensive | yes | yes | diffuse |
| 68 | 25 | M | PA | I | Resection | extensive | extensive | yes | no | diffuse |
| 70 | 14 | M | PA | I | Resection | extensive | extensive | yes | no | diffuse |
| 74 | 52 | M | GB | IV | Resection | extensive | extensive | yes | no | diffuse |
| 81 | 39 | F | OA | II | Resection | extensive | moderate | no | no | evident |
| 84 | 60 | F | GB | IV | Resection | extensive | extensive | yes | no | diffuse |
| 85 | 57 | M | GB | IV | Resection | extensive | extensive | yes | yes | diffuse |
| 88 | 13 | M | OD | II | Resection | moderate | moderate | no | no | diffuse |
| 89 | 76 | F | AA | III | Biopsy | none | moderate | no | no | diffuse |
| 91 | 55 | M | GB | IV | Resection | extensive | extensive | yes | yes | diffuse |
| 92 | 53 | M | GB | IV | Resection | extensive | extensive | yes | yes | diffuse |
| 95 | 68 | M | GB | IV | Resection | extensive | moderate | yes | no | diffuse |
| 96 | 36 | F | OD | II | Biopsy | none | moderate | no | no | diffuse |
| 97* | 6 | F | PA | I | Resection | extensive | extensive | no | no | evident |
| 98 | 36 | F | OA | II | Resection | none | extensive | no | no | diffuse |
| 99 | 61 | M | GB | IV | Resection | extensive | extensive | yes | no | diffuse |
| 101 | 49 | F | GG | II | Resection | extensive | minimal | yes | no | evident |
| 102 | 68 | M | GB | IV | Resection | extensive | moderate | yes | no | diffuse |
| 108 | 59 | M | GB | IV | Resection | extensive | extensive | yes | no | diffuse |
| 109* | 44 | F | OA | II | Resection | none | minimal | no | no | diffuse |
| 117* | 40 | M | OD | II | Resection | extensive | minimal | no | no | diffuse |

TABLE 1-continued

Patent demographics, histological diagnosis, surgical procedure and MR findings.

| Subject | Age (y) | Sex | HD | WHO grade | Surgical procedure | Contrast enhancement | Mass effect | Necrosis | Distant Tumor Foci | Delineation |
|---|---|---|---|---|---|---|---|---|---|---|
| 120 | 28 | M | DA | II | Resection | moderate | extensive | no | no | diffuse |
| 122 | 66 | F | GB | IV | Resection | moderate | moderate | no | no | diffuse |

HD = Histopathological Diagnosis,
GB = Glioblastoma,
DA = Diffuse Astrocytoma,
OA = Oligoastrocytoma,
OD = Oligodendroglioma,
AOD = Anaplastic Oligodendroglioma,
AOA = Anaplastic Oligoastrocytoma,
AA = Anaplastic Astrocytoma,
PA = Pilocytic Astrocytoma,
GG = Ganglioglioma
*HD was obtained prior to MR exam

TABLE 2

Mean values with standard deviations for high- and low-grade gliomas, optimal cut-off values and results of the Mann-Whitney test for the hot-spot method, the WT method and the histogram method.

| | Observer 1 Mean (SD) | Observer 2 Mean (SD) | Observer 3 Mean (SD) | Observer 4 Mean (SD) | Optimal cut-off* (LGG/HGG) | Mann-Whitney P Value (LGG/HGG) |
|---|---|---|---|---|---|---|
| LGG; Hot-spot | 2.85 (1.55) | 3.21 (1.90) | 3.84 (1.48) | 3.08 (1.63) | 4.37-5.53 | <.006 |
| HGG; Hot-spot | 7.04 (3.61) | 5.72 (3.64) | 7.37 (3.37) | 7.49 (4.04) | | |
| LGG; WT | 1.85 (0.53) | 1.79 (0.61) | 1.79 (0.53) | 1.70 (0.53) | 2.20-2.44 | <.001 |
| HGG; WT | 2.98 (0.93) | 3.06 (1.30) | 2.94 (0.96) | 2.70 (0.92) | | |
| LGG; Hist. 5-bins | 0.86 (0.10) | 0.87 (0.12) | 0.87 (0.11) | 0.90 (0.10) | 0.74-0.80 | <.001 |
| HGG; Hist. 5-bins | 0.62 (0.17) | 0.65 (0.18) | 0.66 (0.17) | 0.39 (0.10) | | |
| LGG; Hist. 10-bins | 0.59 (0.13) | 0.63 (0.16) | 0.63 (0.15) | 0.65 (0.15) | 0.47-0.51 | <.001 |
| HGG; Hist. 10-bins | 0.39 (0.10) | 0.39 (0.12) | 0.41 (0.12) | 0.43 (0.14) | | |
| LGG; Hist. 15-bins | 0.49 (0.11) | 0.50 (0.13) | 0.50 (0.12) | 0.52 (0.11) | 0.37-0.41 | <.001 |
| HGG; Hist. 15-bins | 0.29 (0.09) | 0.29 (0.10) | 0.31 (0.11) | 0.31 (0.12) | | |
| LGG; Hist. 25-bins | 0.34 (0.10) | 0.36 (0.13) | 0.37 (0.13) | 0.39 (0.13) | 0.24-0.28 | <.001 |
| HGG; Hist. 25-bins | 0.19 (0.07) | 0.19 (0.07) | 0.20 (0.08) | 0.21 (0.09) | | |
| LGG; Hist. 35-bins | 0.28 (0.10) | 0.29 (0.12) | 0.30 (0.13) | 0.31 (0.12) | 0.19-0.26 | <.001 |
| HGG; Hist. 35-bins | 0.14 (0.05) | 0.14 (0.05) | 0.15 (0.06) | 0.15 (0.07) | | |
| LGG; Hist. 50-bins | 0.21 (0.08) | 0.22 (0.09) | 0.23 (0.10) | 0.24 (0.10) | 0.14-0.15 | <.001 |
| HGG; Hist. 50-bins | 0.10 (0.04) | 0.11 (0.04) | 0.11 (0.04) | 0.12 (0.05) | | |
| LGG; Hist. 100-bins | 0.13 (0.07) | 0.13 (0.07) | 0.14 (0.08) | 0.15 (0.08) | 0.08-0.09 | <.001 |
| HGG; Hist. 100-bins | 0.06 (0.02) | 0.06 (0.02) | 0.06 (0.03) | 0.06 (0.03) | | |

LGG = Low-Grade Gliomas,
HGG = High-Grade Gliomas,
SD = Standard deviation
*Range of values derived from binary logistic regression

TABLE 3

Sensitivity and specificity values, inter-observer agreement percentage and Mann-Whitney test results for the hot-spot method, the WT method and the histogram method.

| | Sensitivity* (%) | Specificity* (%) | Agreement** (%) | Mann-Whitney Grade III/IV | Mann-Whitney Oligo/Astro*** |
|---|---|---|---|---|---|
| Hot-spot method (opt. cut-off value) | 55-75 | 81-94 | 68 | .010 < P > .457 | |
| WT method | 61-80 | 72-88 | 82 | .036 < P > .054 | .422 < P > .842 |
| Histogram 5-bins | 57-77 | 76-90 | 80 | .010 < P > .022 | .592 < P > .895 |
| Histogram 10-bins | 68-86 | 63-84 | 70 | .008 < P > .038 | .737 < P > .895 |
| Histogram 15-bins | 63-82 | 71-87 | 84 | .003 < P > .008 | .255 < P > .948 |
| Histogram 25-bins | 69-87 | 68-85 | 82 | .001 < P > .008 | .180 < P > .842 |
| Histogram 35-bins | 70-87 | 72-88 | 72 | .000 < P > .008 | .141 < P > .463 |
| Histogram 50-bins | 70-87 | 73-89 | 80 | .000 < P > .008 | .203 < P > .641 |
| Histogram 100-bins | 74-90 | 77-91 | 88 | .000 < P > .001 | .141 < P > .505 |
| Hot-spot (1.75 cut-off value) | 92-99 | 14-30 | 78 | — | — |

*Range defined by 95 percent confidence intervalls
**Percent of total patient population in which all observers reported the same grading result
***Grade II oligodendroglial tumors vs grade II astrocytomas

The invention claimed is:

1. A computer implemented method for grading malignancy of a tumor, comprising
receiving electronic data comprising a map of values defining perfusion, blood volume, or cellular metabolism in a tumor of a subject;
storing in an electronic memory, a plurality of value intervals, and counting with an electronic processor the number of values within selected regions of the map that are within each of a plurality of defined value intervals to determine a frequency distribution of values in the selected regions;
assessing a tumor malignancy based on the frequency distribution, where a more heterogeneous distribution corresponds to a higher malignancy; and
transmitting tumor assessment data based, at least in part, on the assessment of the tumor malignancy to an output device.

2. The method according to claim 1, wherein the tumor malignancy assessment is based on one or more of the following parameters determined from the frequency distribution:
a parameter descriptive of a shape of the frequency distribution,
variables in a parametric model applied to the frequency distribution;
a highest relative fraction of values in one interval;
whether the distribution exceeds a predetermined threshold value; or
a FWHM or similar value of the frequency distribution.

3. The method according to claim 1, wherein the map of values is a blood volume map obtained by perfusion imaging using an intravascular contrast agent.

4. The method according to claim 1, wherein the map of values is a glucose metabolism map obtained by positron emission tomography (PET).

5. The method according to claim 1, wherein assessing the tumor malignancy comprises determining a shape of the frequency distribution and comparing with previously determined shapes of equivalent frequency distributions from tumors with a known malignancy assessment.

6. The method according to claim 1, wherein the entire tumor is selected to be applied in the malignancy assessment.

7. The method according to claim 1, further comprising normalizing the frequency distribution to enable comparison between frequency distributions of different tumors.

8. The method of claim 1, further comprising selecting regions of the tumor whose corresponding values in the map are to be applied in the grading.

9. The method according to claim 8, further comprising normalizing or standardizing values of at least the selected regions of the tumor to a reference value.

10. The method of claim 1, wherein the output device is an electronic display, a printer, a data bus, or a network connection.

11. The method of claim 1, further comprising receiving tumor image data from an input device, wherein the map of values is derived from the tumor image data.

12. The method of claim 11, wherein the tumor image data is generated by a CT, MR, or PET scanner.

13. A system for grading malignancy of tumors, the system comprising:
a receiver configured to receive a map of values defining perfusion, blood volume, or cellular metabolism of a tumor of a subject;
software configured to co-register the map of values with image data representing tissue type of a tumor region;
a data selection tool configured to electronically assist an operator in selecting regions of the tumor whose corresponding values in the map are to be applied in the grading;
software configured to count the number of values of the selected regions within each of a plurality of value intervals to determine a frequency distribution of values in the selected regions;
software for determining one or more parameters from the frequency distribution related to heterogeneity of the frequency distribution; and
a transmitter configured to transmit parameter data derived, at least in part, from the one or more parameters to an output device.

14. The method according to claim 13, wherein the software for determining one or more parameters comprises means for correlating said one or more parameters with a malignancy of the tumor, where the more heterogeneous frequency distribution corresponds to a higher malignancy grade.

15. The system of claim 13, further comprising an image data receiver for receiving tumor image data.

16. The system of claim 15, wherein the tumor image data is generated by a CT, MR, or PET scanner.

17. The system of claim 15, wherein the image data receiver is an image recording apparatus such as a CT, MR, or PET scanner.

18. The system of claim 15, wherein the image data receiver is an internal or external storage.

19. The system of claim 13, wherein the transmitter is configured to transmit data to a printer, a display, a data bus, or a network connection.

20. The system of claim 15, wherein the image data receiver is a data bus allowing access to a memory, an internet connection, or a cable or wireless connection.

21. A method for preparing a correlation data set for use in grading the malignancy of a tumor, comprising:
receiving electronic data comprising a plurality of maps of values defining perfusion, blood volume, or cellular metabolism in a plurality of tumors;
selecting a set of tumors of similar type so that the set comprises tumors of all malignancies;
storing in an electronic memory, a histologically determined malignancy of each tumor in the set;
for each tumor in the set:
selecting regions of the tumor whose corresponding values in the map of values are to be applied in the grading;
storing, in an electronic memory, a plurality of value intervals and counting with a processor circuit, the number of values of the selected regions within each interval to determine a frequency distribution of values in the selected regions;
determining, with a processor circuit, one or more parameters characterizing the heterogeneity of the frequency distribution; and
correlating the determined parameters with the histological determined malignancies to prepare a correlation data set from which a malignancy can be estimated for another tumor of similar type using corresponding parameters obtained from this other tumor.

22. The method of claim 21, further comprising transmitting correlation data derived, at least in part, from the correlation data set to an output device.

23. The method of claim 22, wherein the output device is an electronic display, a printer, a data bus, or a network connection.

24. The method of claim 21, further comprising receiving tumor image data from an input device, wherein the map of values is derived from the tumor image data.

25. The method of claim 24, wherein the tumor image data is generated by a CT, MR, or PET scanner.

* * * * *